US006553588B2

(12) United States Patent
Hensley et al.

(10) Patent No.: US 6,553,588 B2
(45) Date of Patent: Apr. 29, 2003

(54) PEDESTAL GAS, VACUUM AND ELECTRIC DELIVERY SYSTEM

(75) Inventors: David W. Hensley, Milan, IN (US); Linda Williamson, Batesville, IN (US); Airen R. Springer, Versailles, IN (US); Hilary Fullenkamp, Batesville, IN (US); Paul Messerschmidt, Batesville, IN (US); Robert W. Wilson, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 87 days.

(21) Appl. No.: 09/780,764

(22) Filed: Feb. 9, 2001

(65) Prior Publication Data

US 2002/0108177 A1 Aug. 15, 2002

(51) Int. Cl.[7] ................................................ A47B 71/00
(52) U.S. Cl. ............................ 5/600; 5/503.1; 248/127
(58) Field of Search ................... 5/600, 503.1; 248/127

(56) References Cited

U.S. PATENT DOCUMENTS

| | | | | |
|---|---|---|---|---|
| 3,567,842 A | * | 3/1971 | Meyer | 174/48 |
| 3,843,112 A | * | 10/1974 | McDonald | 378/209 |
| 4,988,062 A | * | 1/1991 | London | 128/DIG. 26 |
| 5,323,565 A | * | 6/1994 | Kappers et al. | 174/49 |
| 5,370,111 A | * | 12/1994 | Reeder et al. | 128/202.13 |
| 5,398,359 A | * | 3/1995 | Foster | 248/922 |
| 5,452,807 A | * | 9/1995 | Foster et al. | 211/168 |
| 5,618,090 A | * | 4/1997 | Montague et al. | 211/26 |
| 6,073,284 A | * | 6/2000 | Borders | 5/600 |
| 6,145,253 A | * | 11/2000 | Gallant et al. | 52/220.1 |

OTHER PUBLICATIONS

P683 Service Pedestals, Hill-Rom Brochure, 2000.
EpiCare™ Pedestal Service Manual, Nov., 2000.

* cited by examiner

Primary Examiner—J. J. Swann
Assistant Examiner—Katherine Mitchell
(74) Attorney, Agent, or Firm—Barnes & Thornburg

(57) ABSTRACT

A pedestal apparatus for use with a patient support, such as an x-ray table, provides a plurality of services, such as gas, vacuum and electric power, near a patient supported on the patient support. The apparatus includes a housing having opposite ends, opposite sides, a top and bottom. The opposite sides of the housing are configured to include a plurality of service outlets. The top of the housing is arched to provide an upwardly-facing convex exterior surface, and the top of the housing is formed with axial sides overhanging the opposite sides of the housing.

28 Claims, 3 Drawing Sheets

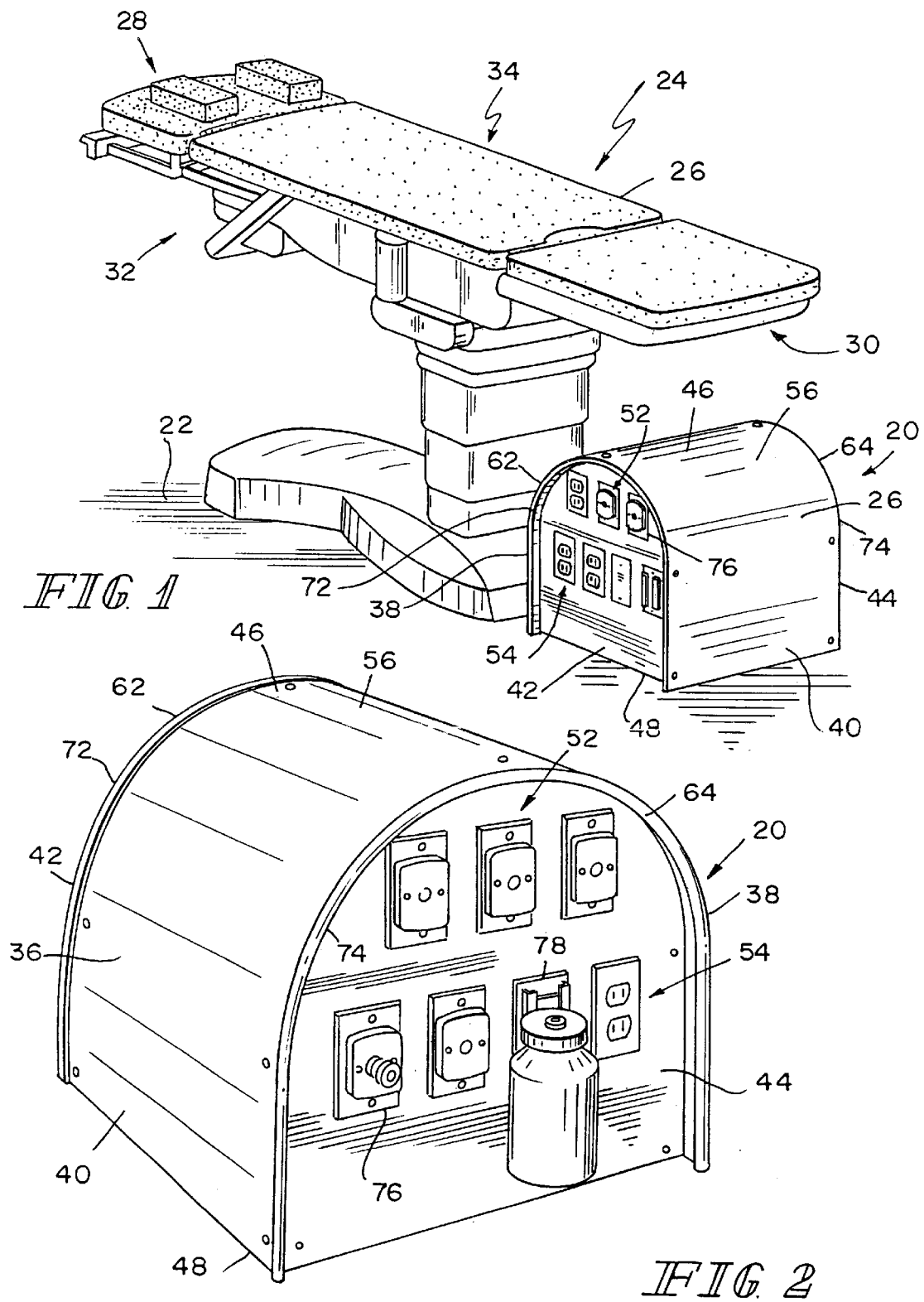

PEDESTAL GAS, VACUUM AND ELECTRIC DELIVERY SYSTEM

BACKGROUND AND SUMMARY OF THE INVENTION

This invention generally relates to a medical gas, vacuum and electric delivery system for medical facilities, such as hospitals. More particularly, this invention relates to a pedestal for use with a patient support, such as an x-ray table or an operating table, to provide a plurality of services, such as medical gas, vacuum and electric power, near a patient to be treated on the patient support.

Hospital head wall systems are well known in the industry. Head wall systems are used in hospitals for providing medical gas (hereinafter referred to as gas), vacuum and electric services near a patient to be treated on a patient support. Head wall systems are typically mounted on walls behind hospital beds, nursing beds and intensive care beds where such services are often required. Conventional head wall designs include electric outlets and fixed or movable gas and vacuum outlets for supplying normal and emergency power, air, oxygen, vacuum, or other gases to hospital rooms. In conventional head wall designs, movable gas outlets slide on raceways formed on the head wall. Gas, vacuum and electric supply lines are coupled to the respective outlets. The gas, vacuum and electric supply lines are concealed behind a front panel of the head wall. See, for example, U.S. Pat. No. 6,145,253, issued on Nov. 14, 2000, and entitled "Head Wall for a Hospital Room", contents of which are incorporated herein by reference.

This invention relates to floor-mounted pedestals, which like head walls, are used in hospitals for providing a plurality of services, such as gas, vacuum and electric power, near a patient undergoing a surgery or a procedure on a patient support, such as a surgery table in an operating room or an x-ray table in a cath lab. Pedestals are typically mounted on hospital floors near the equipment where such services are needed. For example, a pedestal is placed under a catheterization or an xray table in a cath lab procedural room (sometimes referred to herein as cath lab or catheterization lab) to supply gas, vacuum and electric services near a patient to be treated on the x-ray table. Some examples of procedures performed in the cath lab, but not totally inclusive, are balloon angioplasty, angiograms and stent procedures. A cath lab is generally located near the operating rooms in hospitals so that a patient undergoing a cardiac procedure can be quickly moved to an operating room, if needed, in the event of an emergency.

Conventional pedestal designs include a plurality of gas, vacuum and electric outlets for supplying oxygen, medical air, other gases, vacuum, normal power and emergency power. Examples of other gases include nitrous oxide, nitrogen, helium and carbon dioxide. Pedestals typically include a housing having opposite laterally-extending ends, opposite longitudinally-extending sides, a top and bottom defining an interior region. The opposite sides and ends of the housing are configured to include a plurality of electric, gas and vacuum outlets. A plurality of hospital gas, vacuum and electric supply lines enter the interior region of the floor-mounted pedestal through an opening in the bottom of the housing. A plurality of hoses couple the gas and vacuum supply lines to the respective gas and vacuum outlets. A plurality of cables couple the electric supply lines to the respective electric outlets. An example of such pedestal is EpiCare Pedestal, Model No. P683A01, marketed by Hill-Rom, Inc. EpiCare is a registered trademark of Hill-Rom, Inc.

As used in this description and claims, the phrase "gas, vacuum and electric services" shall be construed to mean just gas service, just vacuum service, just electric service, or any combination of these services. For example, a pedestal may be used to provide just gas and vacuum services near an x-ray table, or just normal and emergency electric services near an x-ray table or all of gas, vacuum and electric services near an x-ray table. Similarly, the phrase "gas, vacuum and electric outlets" shall be construed to mean just gas outlets, just vacuum outlets, just electric power outlets, or any combination of these outlets. Thus, the phrase "gas, vacuum and electric" is not to be construed as a limitation in any way. Instead, the phrase "gas, vacuum and electric" is understood to mean one or more of these services to suit the requirements for various utilities at a particular station in a hospital.

In accordance with the present invention, a pedestal for use with a patient support, such as an x-ray table, provides gas, vacuum and electric services near a patient supported on the patient sup port. The pedestal includes a housing having opposite laterally-extending ends, opposite longitudinally-extending sides, a top and bottom. The opposite sides of the housing are configured to include a plurality of gas, vacuum and electric outlets, and the top of the housing is arched to provide an upwardly-facing convex exterior surface. According to another feature of the present invention, the top is formed with axial sides overhanging the opposite sides of the housing.

Additional features and advantages of the invention will become apparent to those skilled in the art upon consideration of the following detailed description of the illustrated embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a pedestal in accordance with the present invention, the pedestal being shown mounted on the floor under an x-ray table in a cath lab, the pedestal including a housing having opposite laterally-extending ends, opposite longitudinally-extending sides, a top and bottom, the opposite sides of the housing being configured to include a plurality of gas, vacuum and electric outlets so that a caregiver can have access to the gas, vacuum and electric outlets from either side of the x-ray table, the top of the pedestal housing being configured to provide an upwardly-facing convex exterior surface, the upwardly-facing convex exterior surface of the housing having axial sides extending beyond the opposite sides of the housing, FIG. 2 is an enlarged perspective view of the FIG. 1 pedestal showing a plurality of gas, vacuum and electric outlets on one side of the housing, and also showing a bottle slide supporting a bottle for body fluids, the opposite side of the housing also having a plurality of gas, vacuum and electric outlets.

DETAILED DESCRIPTION OF DRAWINGS

Figure 3:
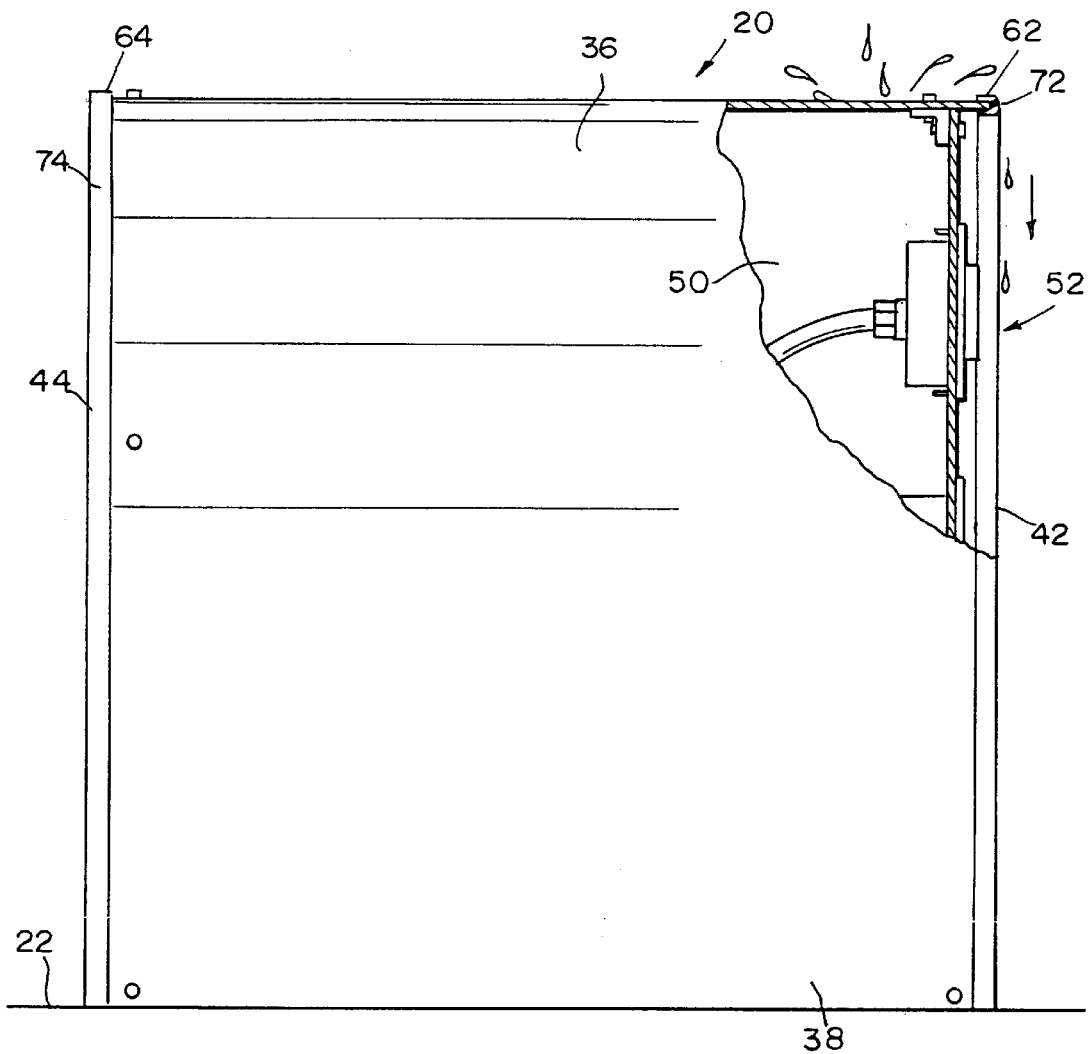
FIG. 3 is an end view of the pedestal of FIGS. 1 and 2 with portions broken away to show the interior of the pedestal housing, and showing a hose coupled to the backbody of a gas outlet mounted to a side wall of the pedestal housing, and showing bumpers coupled to the axial sides overhanging the opposite sides of the pedestal housing.

Referring now to the drawings, FIG. 1 illustrates a pedestal 20 mounted on the floor 22 in a cath lab under an x-ray table 24 to provide gas, vacuum and electric services near a patient undergoing a procedure on the x-ray table 24. The x ray table 24 includes a deck 26 having a transversely-extending head end 28, a transversely-extending foot end 30 and opposite longitudinally-extending sides 32, 34 extending between the head and foot ends 28, 30. As shown in FIGS. 1–4, the pedestal 20 includes a shell or housing 36 having opposite transversely-extending ends 38 and 40, opposite longitudinally-extending sides 42 and 44, a top 46 and a bottom 48 defining an interior region 50. The opposite sides 42, 44 of the pedestal housing 36 are configured to include a plurality of gas, vacuum outlets 52 and a plurality of electric outlets 54. The top 46 of the housing 36 is arched to provide an upwardlyfacing convex exterior surface 56. The arched top 46 prevents objects or materials from being placed thereon, and provides better egress to spilled liquids. Illustratively, the upwardly-facing top surface 56 is a curved surface formed as an arch about a transverse or lateral axis extending between the opposite sides 42, 44 of the pedestal housing 36. As shown in FIG. 3, the upwardly-facing top surface 56 is configured to include axial sides 62, 64 overhanging the opposite sides 42, 44 of the pedestal housing 36. The overhanging opposite sides 62, 64 of the pedestal housing 36 protect the gas, vacuum and electric outlets 52, 54 from physical damage and spilled fluids.

Protective rubber bumpers 72, 74 are coupled to the axial sides 62, 64 of the pedestal housing 36. The bumpers 72, 74 not only protect the caregiver from injury, but they also serve as fluid directional gutters to direct spilled fluids away from the gas, vacuum and electric outlets 52, 54 as shown in FIG. 3.

As previously described, the phrase "gas, vacuum and electric services" as used in this description and claims, shall be construed to mean just gas service, just vacuum service, just electric service, or any combination of these services. For example, a pedestal may be used to provide just gas and vacuum services near an x-ray table, or just normal and emergency electric services near an xray table or all of gas, vacuum and electric services near an x-ray table. Similarly, the phrase "gas, vacuum and electric outlets" shall be construed to mean just gas outlets, just vacuum outlets, just electric power outlets, or any combination of these outlets. Thus, the phrase "gas, vacuum and electric" is not to be construed as a limitation in any way. Instead, the phrase "gas, vacuum and electric" is understood to mean one or more of these services depending on the needs of a customer.

The opposite sides 42, 44 of the pedestal housing 36 are configured to include a plurality of cutouts 76 for receiving the plurality of electric, gas and vacuum outlets 52, 54. Illustratively, there are a total of fourteen cutouts 76, seven cutouts 76 on each of the opposite sides 42, 44. The seven cutouts 76 on each side 42, 44 are arranged in two rows of three and four cutouts 76 so that the cutouts 76 in the two rows are offset with respect to each other to provide better access to individual outlets. Preferably, all the cutouts 76 are of the same size so that the pedestal 20 can be customized or reconfigured to suit the requirements for various utilities at a particular station in a hospital. Interchangeability of the outlets 52, 54 gives the ability to quickly add or relocate the service outlets as various needs arise.

As shown in FIG. 2, one of the cutouts 76 on the second side 44 of the pedestal 20 is equipped with a bottle slide 78 for supporting a bottle for body fluids.

All the electric outlets 54 may be placed on one side of the pedestal 20, and all the gas and vacuum outlets 52 may be placed on the other side of the pedestal 20 to increase separation between the live electrical wires and tubes carrying oxygen. Minimum 8 inches (about 20 centimeters) of clearance is recommended between the electric and oxygen lines to minimize fire hazard. The pedestal 20 is mounted on the floor 22 such that the longitudinally-extending sides 42, 44 of the pedestal 20 are generally parallel to longitudinally-extending sides 32, 34 of the x-ray table 24. This allows the caregiver to have access to the service outlets 52, 54 from either side of the x-ray table 24.

Figure 5:
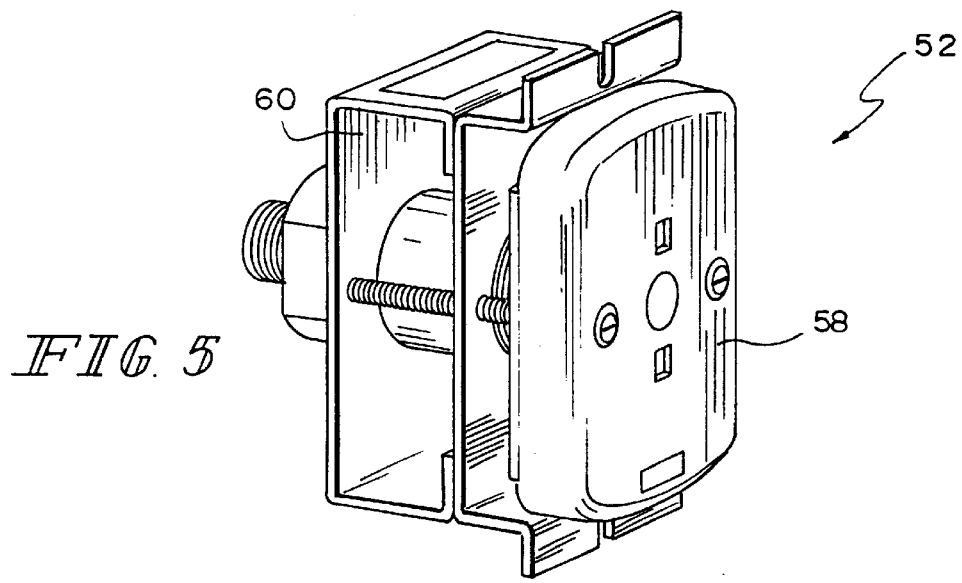
FIG. 5 is a perspective view of a Diamond(& key style gas/vacuum outlet including a frontbody assembly configured to be coupled to a patient treatment device and a backbody assembly configured to be mounted to a side wall of the pedestal housing and coupled to the facility's medical gas/vacuum distribution system.

The gas, vacuum and electric outlets 52, 54 are color coded and labeled for quick visual identification thereof, and to reduce the risk of connection errors. For example, oxygen outlet is green, medical air outlet is yellow, nitrous oxide outlet is blue, nitrogen outlet is purple, vacuum outlet is white, normal power outlet is ivory and emergency power outlet is red. Typically, as shown in FIG. 5, the gas and vacuum outlets 52 comprise a frontbody assembly 58 configured to be coupled a patient care system and a backbody or rough-in assembly 60 configured to be coupled to the facility's piped medical gas/vacuum system. The frontbody system 58 includes a primary check valve and a keying disc. The keying disc contains a gas specific keying system which prevents cross-connection from the frontbody assembly 58 to a patient care system and from the frontbody assembly 58 to the backbody assembly 60. The primary check valve prevents gas flow when a patient care system is removed from the frontbody assembly 58. The backbody assembly 60 contains a secondary check valve for pressurized medical gases. The secondary check valve prevents gas flow when the frontbody assembly 58 is removed from the backbody assembly 60 for repair or maintenance.

The gas and vacuum outlets 52 may be of the type marketed by Hill-Rom, Inc. under the Hill-Rom Diamond-Care and Diamond trademarks. These outlets 52 are available in any of the four major key styles: Hill-Rom Diamond, Chemetron, Puritan-Bennett and DISS. Diamond and DiamondCare are trademarks of Hill-Rom MEDAES, Inc. Chemetron is a trademark of Allied Healthcare Products, Inc. Puritan-Bennett is a trademark of Puritan-Bennett Corporation. The electric outlets 54 are conventional.

Typically, the hospital floors are provided with underground trenches or channels (not shown) to run utility services to the locations where such services are needed. The underground trenches keep the utility supply lines out of sight to provide a clean esthetically-appealing environment. Prior to installation of the pedestal 20, the gas and vacuum supply and electric power to the cath lab procedural room is disabled.

Figure 4:
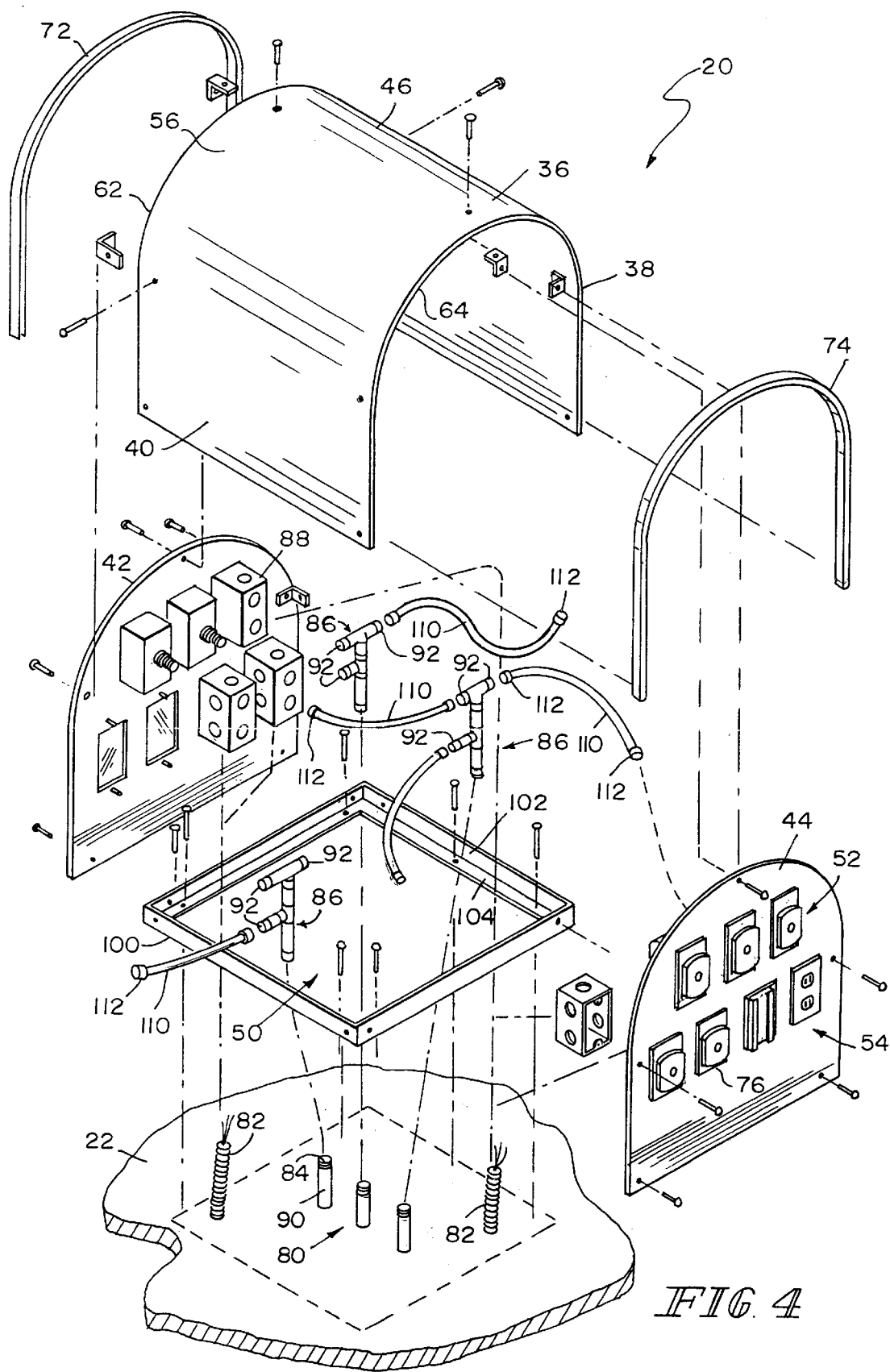
FIG. 4 is an exploded perspective view of the FIG. 1 pedestal showing the riser tubes configured to be coupled to the facility gas and vacuum supply lines, electric conduits configured to be coupled to the facility normal and emergency power lines, manifold assemblies configured to be coupled to the gas and vacuum riser tubes, supply hoses with fittings configured to be coupled to the gas and vacuum manifold assemblies and the backbody assemblies of the gas and vacuum outlets, and a pedestal mounting frame configured to be mounted on the floor.

Referring to FIG. 4, a template (not shown) supplied with the pedestal 20 is used to mark holes on the floor 22 for gas and vacuum riser tubes, electric conduits, and for mounting the pedestal 20. Holes are then drilled in the concrete floor 22 of the cath lab procedural room using suitable equipment, such as a hammer drill. Floor-to-floor fire barrier is installed after drilling holes in the concrete floor 22.

Riser tubes 80 and electric conduits 82 are then installed as shown in FIG. 4. The riser tubes 80 are coupled to the facility gas and vacuum supply lines, and electric conduits 82 are coupled to the facility normal and emergency power lines. Disposable plastic protective caps 84 are used to cap the riser tubes 80 to keep the debris out of the riser tubes 80 prior to installation of the manifold assemblies 86. The riser tubes 80 and electric conduits 82 extend above the floor 22 generally at right angles thereto a short distance at a location where gas, vacuum and electric services are needed. Illustratively, the riser tubes 80 and the electric conduits 82 extend above the floor 22 about 4 inches. Typically, the riser tubes 80 are made from copper tubing, and electric conduits 82 are made from zinc plated steel tubing. The copper riser tubes 80 are isolated from the concrete floor using individual 1 to 1.25 inch (about 3 centimeters) diameter PVC pipes 90.

To continue installation, the plastic protective caps 84 on the riser tubes 80 are removed, and manifold assemblies 86 with appropriate check valves 92 are installed on the gas and vacuum riser tubes 80. As is the practice in the industry, installation of the gas and vacuum riser tubes 80 and manifold assemblies 86 should be done by a certified brazier, and installation of electric wiring and conduits 82 should be done by a certified electrician in accordance with applicable codes.

A generally rectangular, pedestal mounting frame or base angle 100 is placed on the concrete floor 22 so that the pedestal mounting holes in the floor 22 are aligned with the corresponding holes 102 in the pedestal mounting frame 100. Typically, the pedestal mounting holes in the concrete floor 22 are drilled at the same time holes are drilled for the gas and vacuum riser tubes 80 and for electrical conduits 82. The pedestal mounting frame 100 is then secured to the floor 22 using suitable fastening means, such as screws or concrete anchors. The pedestal mounting frame 100 is configured to form a well 104 for receiving the pedestal housing 36.

A plurality of supply hoses 110 with appropriate fittings 112 couple the manifold assemblies 86 to the respective gas and vacuum outlets 52. Likewise, a plurality of cables (not shown) couple the electrical conduits 82 to the electric outlets 54. The bottom 48 of the pedestal housing 36 is open so that the riser tubes 80, electric conduits 82, supply hoses 110 and electric cables can enter the interior region 50 of the pedestal housing 36 therethrough. Various connections are tested for leakage. The pedestal housing 36 is placed in the well 104 of the pedestal mounting frame 100. The pedestal housing 36 is then secured to the pedestal mounting frame 100 using suitable fastening means, such as screws. The gas, vacuum and electric services to the cath lab procedural room are then restored. The riser tubes 80, electrical conduits 82, the manifold assemblies 86, the gas and vacuum outlets 52, electric outlets 54, the supply hoses 110 and electric cables are all preferably color coded and labeled per the industry standard to avoid connection errors.

Illustrative dimensions of the pedestal 20 are: a) longitudinal dimension is about 18 inches (approximately 46 centimeters), b) transverse dimension is about 20 inches (approximately 51 centimeters), c) the vertical dimension or the height is about 18 inches (approximately 46 centimeters), d) the radius of the arched top is about 10 inches (approximately 25 centimeters), and e) the axial overhang is about 1 inch (approximately 2.54 centimeters) on each side. Illustratively, the material of the pedestal 20 is stainless steel.

Although the invention has been described in detail with reference to a certain illustrated embodiment, variations and modifications exist within the scope and spirit of the invention as described and as defined in the following claims.

What is claimed is:

1. A pedestal apparatus for use with a patient support to provide a plurality of services near a patient to be treated on the patient support, the apparatus comprising a housing having opposite ends, opposite sides, a top and a bottom defining an interior region, the opposite sides including a plurality of service outlets, the opposite ends not including any service outlets, wherein the service outlets include gas, vacuum and electric outlets, wherein all the electric outlets are placed on one side of the apparatus, and wherein all the gas outlets are placed on the other side of the apparatus, and the top being formed with axial sides overhanging the opposite sides of the housing.

2. The apparatus of claim 1, wherein the top of the housing is arched to provide an upwardly-facing convex exterior surface.

3. The apparatus of claim 1, wherein the top of the housing is a curved surface formed as an arch about an axis extending between the opposite sides.

4. The apparatus of claim 1, wherein the top axial sides are covered with resilient material.

5. The apparatus of claim 1, wherein the patient support includes a deck having a head end, a foot end and opposite sides extending between the head and foot ends, and wherein the apparatus is placed under the deck such that opposite sides of the apparatus are generally parallel with the opposite sides of the deck.

6. The apparatus of claim 1, for use with a plurality of supply lines entering the interior region of the housing through an opening in the bottom of the housing, and wherein the plurality of supply lines are coupled to the respective plurality of service outlets.

7. The apparatus of claim 6, wherein the plurality of supply lines and outlets are color coded.

8. The apparatus of claim 1, wherein the plurality of outlets are color coded.

9. The apparatus of claim 1, wherein the sides of the housing include a plurality of cutouts for the plurality of service outlets, and wherein all the cutouts are of the same size.

10. A pedestal apparatus for use with a patient support to provide a plurality of services near a patient to be treated on the patient support, the apparatus comprising a housing having opposite ends, opposite sides, a top and bottom defining an interior region, the opposite sides including a plurality of service outlets, wherein the top of the housing is arched to provide an upwardly-facing convex exterior surface having a uniform cross section from one side of the housing to the opposite side of the housing, wherein all the electric outlets are placed on one side of the apparatus, and wherein all the gas outlets are placed on the other side of the apparatus, and wherein the top is formed with axial sides overhanging the opposite sides of the housing.

11. The apparatus of claim 10, wherein the top axial sides are covered with resilient material.

12. The apparatus of claim 10, wherein the patient support includes a deck having a head end, a foot end and opposite sides extending between the head and foot ends, and wherein the apparatus is placed under the deck such that opposite sides of the apparatus are generally aligned with the opposite sides of the deck.

13. The apparatus of claim 10, for use with a plurality of supply lines entering the interior region of the housing through an opening in the bottom of the housing, and wherein the plurality of supply lines are coupled to the respective plurality of service outlets.

14. The apparatus of claim 13, wherein the plurality of supply lines and outlets are color coded.

15. The apparatus of claim 10, wherein the plurality of outlets are color coded.

16. The apparatus of claim 10, wherein the sides of the housing include a plurality of cutouts for the plurality of service outlets, and wherein all the cutouts are of the same size.

17. The apparatus of claim 10, wherein the top of the housing is a curved surface formed as an arch about an axis extending between the opposite sides.

18. A pedestal for use with a patient support to provide a plurality of services near a patient to be treated on the patient support, the pedestal comprising a housing having opposite ends, opposite sides, a top and a bottom defining an interior region, the opposite sides having a plurality of service outlets, the opposite ends and the top being free of any service outlets and wherein the service outlets include gas, electric outlets, and wherein all the electric outlets are placed on one side of the pedestal, and wherein all the gas outlets are placed on the other side of the pedestal.

19. The pedestal of claim 18, wherein the opposite ends and the top of the housing form a continuous arch having a uniform cross section from one side of the housing to the opposite side of the housing.

20. The pedestal of claim 19, wherein the continuous arch is formed with axially-extending sides overhanging the opposite sides of the housing.

21. The pedestal of claim 20, wherein the axially-extending overhanging sides are covered with resilient material.

22. The pedestal of claim 18, wherein the patient support includes a deck having a head end, a foot end and opposite sides extending between the head and foot ends, and wherein the pedestal is placed under the deck such that the pedestal is placed within a footprint of the deck and such that the opposite sides of the pedestal are generally parallel with the opposite sides of the deck.

23. The pedestal of claim 18, wherein the pedestal is supported on a floor.

24. A pedestal for use with and separate from a patient support to provide a plurality of services near a patient to be treated on the patient support, the pedestal comprising a housing having opposite ends, opposite sides, a top and a bottom defining an interior region, the opposite sides having a plurality of service outlets, wherein the service outlets include gas, electric outlets, and wherein all the electric outlets are placed on one side of the pedestal, and wherein all the gas outlets are placed on the opposite side of the pedestal, and the opposite ends and the top of the housing forming a continuous arch having a uniform cross section from one side of the housing to the opposite side of the housing.

25. The pedestal of claim 24, wherein the continuous arch is formed with axially-extending sides overhanging the opposite sides of the housing.

26. The pedestal of claim 25, wherein the axially-extending overhanging sides are covered with resilient material.

27. The pedestal of claim 25, wherein the patient support includes a deck having a head end, a foot end and opposite sides extending between the head and foot ends, and wherein the pedestal is placed under the deck such that the pedestal is placed within a footprint of the deck and such that opposite sides of the pedestal are generally parallel with the opposite sides of the deck.

28. A pedestal for use with and separate from a patient support to provide a plurality of services near a patient to be treated on the patient support, the pedestal comprising a housing having opposite ends, opposite sides, a top and a bottom defining an interior region, the opposite sides having a plurality of service outlets, wherein the service outlets include gas, electric outlets, and wherein all the electric outlets are placed on one side of the pedestal, and wherein all the gas outlets are placed on the opposite side of the pedestal, the top of the housing forming an arch having a uniform cross section from one side of the housing to the opposite side of the housing.

* * * * *